United States Patent

Ozeki et al.

[11] Patent Number: 5,246,929
[45] Date of Patent: Sep. 21, 1993

[54] NAPHTHO THIAZINE (OR OXALINE) DERIVATIVES AND PREPARATIONS THEREOF

[75] Inventors: Masakatsu Ozeki, Wako; Shin-ichi Kodato; Kousuke Yasuda, both of Kounosu; Yukitsuka Kudo, Kyoto; Kayoko Maeda, Osaka, all of Japan

[73] Assignee: Tanabe Seiyaku Co., Ltd., Osaka, Japan

[21] Appl. No.: 648,891

[22] Filed: Jan. 31, 1991

[30] Foreign Application Priority Data

Feb. 8, 1990 [JP] Japan .................. 2-31068
Mar. 7, 1990 [JP] Japan .................. 2-56220
Mar. 9, 1990 [JP] Japan .................. 2-59328

[51] Int. Cl.$^5$ .................. A61K 31/54; C07D 279/22; C07D 265/38
[52] U.S. Cl. .................. 514/224.5; 514/229.8; 544/32; 544/73; 544/101
[58] Field of Search .................. 544/52, 56, 58.4, 105, 544/32, 73, 101; 514/227.5, 227.8, 230.5, 224.5, 229.8

[56] References Cited

U.S. PATENT DOCUMENTS

| | | | |
|---|---|---|---|
| 3,143,545 | 4/1964 | Lowrie et al. | 544/52 |
| 3,395,150 | 7/1968 | Krapcho | 540/468 |
| 3,547,915 | 12/1970 | Bub | 544/105 |
| 3,681,330 | 8/1972 | Pesson | 544/73 |
| 3,705,894 | 12/1972 | Gerzon et al. | 548/253 |
| 3,748,321 | 7/1973 | Krapcho | 540/476 |
| 3,879,522 | 4/1975 | Pesson | 514/230.5 |
| 4,107,167 | 8/1978 | Lorenz et al. | 546/335 |
| 4,534,300 | 4/1986 | Iwao et al. | 514/225 |

FOREIGN PATENT DOCUMENTS 0116368 8/1984 European Pat. Off. .
2332756 6/1977 France .
1173942 12/1969 United Kingdom .

OTHER PUBLICATIONS

Iwao et al.; "Chemical Abstract", vol. 104(13), 1985, #109666P.

Iwao et al., "Chemical Abstract", vol. 102(3) 1984, #24637P.

Abstract of Japan 60-166674 (A), vol. 10, No. 13(C-323) (2070), Jan. 1986.

G. R. Clemo et al., Journal of the Chemical Society Transactions; vol. 121, pp. 642-649, (1922).

Primary Examiner—Mukund J. Shah
Assistant Examiner—Y. N. Gupta
Attorney, Agent, or Firm—Birch, Stewart, Kolasch & Birch

[57] ABSTRACT

Thiazine (or oxazine) derivatives of the formula [I]:

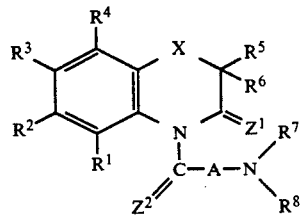

wherein $R^1$ and $R^2$ are both H or form a naphthalene ring together with the benzene ring; $R^3$ and $R^4$ are both H, or one of them is halogen and another is H; X is S or O; $R^5$ and $R^6$ are each i) H, ii) lower alkyl, iii) cycloalkyl, iv) substituted phenyl, v) naphthyl, vi) lower alkyl which is substituted by substituted or unsubstituted phenyl, or vii) S-containing heterocyclic group; one of $Z^1$ and $Z^2$ is O and another is H$_2$; A is lower alkylene; $R^7$ and $R^8$ are each i) H, ii) lower alkyl, iii) lower alkenyl, iv) lower alkynyl, or v) lower alkyl which is substituted by substituted or unsubstituted phenyl, or both form together N-containing heterocyclic group; provided that when both of $R^1$ and $R^2$ are H, $Z^2$ is O and either one of $R^5$ and $R^6$ is substituted phenyl, naphthyl or S-containing heterocyclic group, or their salts, which have calcium antagonistic activity within the cerebral tissues and are useful for prophylaxis and treatment of ischemic encephalopathia and/or cerebral neurocyte dyscrasia, and process for preparing said compounds.

12 Claims, No Drawings

NAPHTHO THIAZINE (OR OXALINE) DERIVATIVES AND PREPARATIONS THEREOF

TECHNICAL FIELD

This invention relates to novel thiazine (or oxazine) derivatives useful for the prophylaxis and treatment of ischemic encephalopathia and/or cerebral neurocyte dyscrasia, and processes for preparing the same.

PRIOR ART

Hemokinetic dyscrasia due to intracephalic hemorrhage or thromboembolia induces shortage of glucose and oxygen etc. which are source of energy for neurocytic activity and then induces nervous cellular necrosis at the ischemic lesion site. For treating such ischemic encephalopathia, there has hitherto been used a medicament such as flunarizine dihydrochloride which can increase cerebral blood flow and can promote supplement of glucose and oxygen etc. to the ischemic lesion site.

Besides, it has recently been clarified that calcium participates in cellular injury in ischemia and that the cellular injury in ischemia can be prevented by inhibiting the flow of calcium into neurocytes (cf. Trends in Pharmacological Science, 1989, 10, 397). Thus, it has been desired very much to develop a calcium antagonistic agent which can directly act on the cerebral cells.

SUMMARY DESCRIPTION OF THE INVENTION

An object of this invention is to provide novel compounds which have excellent calcium antagonistic activity within the cerebral tissues and are useful for the prophylaxis and treatment of ischemic encephalopathia and/or cerebral neurocyte dyscrasia.

DETAILED DESCRIPTION OF THE INVENTION

The novel compounds of this invention are thiazine (or oxazine) derivative of the following formula [I]:

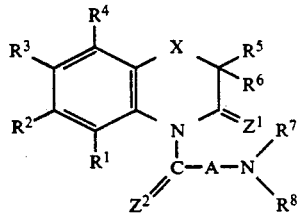

[I]

wherein $R^1$ and $R^2$ are both hydrogen atom or form a naphthalene ring together with the benzene ring; $R^3$ and $R^4$ are both hydrogen atom, or one of them is a halogen atom and another is hydrogen atom; X is sufur atom or oxygen atom; $R^5$ and $R^6$ are the same or different and are each i) hydrogen atom, ii) a lower alkyl, iii) a cycloalkyl, iv) a substituted phenyl, v) naphthyl, vi) a lower alkyl which is substituted by a substituted or unsubstituted phenyl, or vii) a sulfur-containing monoheterocyclic group; one of $Z^1$ and $Z^2$ is oxygen atom and another is two hydrogen atoms; A is a lower alkylene; $R^7$ and $R^8$ are the same or different and are each i) hydrogen atom, ii) a lower alkyl, iii) a lower alkenyl, iv) a lower alkynyl, or v) a lower alkyl which is substituted by a substituted or unsubstituted phenyl, or both form together with the adjacent nitrogen atom a nitrogen-containing monoheterocyclic group; provided that when both of $R^1$ and $R^2$ are hydrogen atom, $Z^2$ is oxygen atom and either one of $R^5$ and $R^6$ is a substituted phenyl, naphthyl or a sulfur-containing monoheterocyclic group, or a pharmaceutically acceptable salt thereof.

In the compounds of the formula [I], the lower alkyl, lower alkylene and lower alkoxy denotes an alkyl, alkylene and alkoxy group having 1 to 6 carbon atoms, preferably 1 to 4 carbon atoms. The lower alkenyl and alkynyl denotes an alkenyl or alkynyl group having 2 to 6 carbon atoms, preferably 2 to 4 carbon atoms. The cycloalkyl denotes a cycloalkyl group having 3 to 8 carbon atoms, preferably 5 to 6 carbon atoms. The sulfur-containing monoheterocyclic group includes, for example, thienyl group, and the subsituted phenyl includes a phenyl group which is substituted by one or two substituents selected from a halogen atom, a trihalogeno(lower)alkyl, a lower alkyl and a lower alkoxy, for example, a halogenophenyl, a dihalogenophenyl, a trihalogeno(lower)alkylphenyl, a lower alkylphenyl, a lower alkoxyphenyl, or di(lower alkoxy)phenyl. The nitrogen-containing monoheterocyclic group includes, for example, imidazolyl, morpholinyl, pyrrolidinyl, piperidinyl, and piperazinyl.

Preferred compounds are compounds of the formula [I] wherein $R^3$ and $R^4$ are both hydrogen atom; one of $R^5$ and $R^6$ is hydrogen atom and another is a halogenophenyl, a trihalogeno(lower)alkylphenyl; A is methylene or ethylene; X is sulfur atom; $R^7$ and $R^8$ are the same or different and are each a lower alkyl.

The compounds [I] of this invention can be prepared by the following processes.

(a) Process A

The compounds [I] are prepared by reacting a compound of the formula:

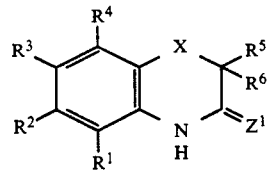

[II]

wherein $R^1$, $R^2$, $R^3$, $R^4$, $R^5$, $R^6$, X and $Z^1$ are as defined above, or a salt thereof with a compound of the formula:

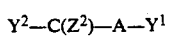

$$Y^2-C(Z^2)-A-Y^1 \quad [III]$$

wherein $Y^1$ and $Y^2$ are the same or different and are each a reactive residue, and A and $Z^2$ are as defined above, to give a compound of the formula:

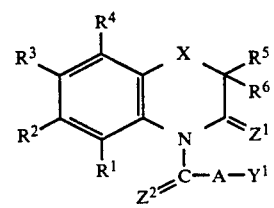

[IV]

wherein $R^1$, $R^2$, $R^3$, $R^4$, $R^5$, $R^6$, X, A, $Z^1$, $Z^2$, and $Y^1$ are as defined above, and then reacting the above compound [IV] with an amine compound of the formula:

 [V]

wherein $R^7$ and $R^8$ are as defined above, or a salt thereof.

(b) Process B

The compounds [I] are prepared by reacting the compound of the formula [II] or a salt thereof with a compound of the formula:

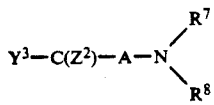 [VI]

wherein $Y^3$ is a reactive residue, and $Z^2$, A, $R^7$ and $R^8$ are as defined above.

(c) Process C

The compounds [I] wherein A is ethylene, $Z^1$ is two hydrogen atom, and $Z^2$ is oxygen atom are prepared by reacting the compound of the formula [II] or a salt thereof with an acrylic acid compound of the formula:

 [VII]

wherein $Y^2$ is as defined above, to give a compound of the formula:

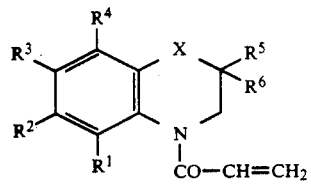 [VIII]

wherein $R^1$, $R^2$, $R^3$, $R^4$, $R^5$, $R^6$, and X are as defined above, and then reacting the above compound [VIII] with an amine compound [V].

(d) Process D

The compounds [I] wherein at least one of $R^7$ and $R^8$ is a lower alkyl, a lower alkenyl, a lower alkynyl, or a lower alkyl which is substituted by a substituted or unsubstituted phenyl are prepared by reacting a compound of the formula:

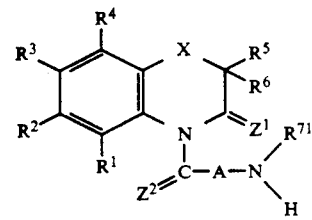 [I-a]

wherein $R^1$, $R^2$, $R^3$, $R^4$, $R^5$, $R^6$, X, A, $Z^1$, and $Z^2$ are as defined above, and $R^{71}$ is hydrogen atom, a lower alkyl, a lower alkenyl, a lower alkynyl, or a lower alkyl which is substituted by a substituted or unsubstituted phenyl, or a salt thereof with a compound of the formula:

$$R^{81}-Y^4 \quad [IX]$$

wherein $R^{81}$ is a lower alkyl, a lower alkenyl, a lower alkynyl, or a lower alkyl which is substituted by a substituted or unsubstituted phenyl, and $Y^4$ is a reactive residue.

In the above reactions, the starting compounds of the formulae [II], [V] and [VI] and the compounds of the formula [I-a] may be used in a free form or in the form of a conventional acid addition salt such as mineral acid salts or organic acid salts. The reactive residues $Y^1$, $Y^2$, $Y^3$ and $Y^4$ includes, for example, a halogen atom (e.g. chlorine atom, bromine atom, etc.), a lower alkylsulfonyloxy, or a lower alkylphenylsulfonyloxy.

The condensation reaction between the compound [II] and the compound [III], the compound [VI], or the acrylic acid compound [VII], and the condensation reaction between the compound [I-a] and the compound [IX] can be carried out in an appropriate solvent in the presence of a base. These reactions proceed at a temperature of from cooling temperature to elevated temperature, preferably 0° to 100° C.

The reaction between the compound [IV] or the compound [VIII] and the amine compound [V] can be carried out in the presence or absence of a base in an appropriate solvent or without solvent. This reaction proceeds at a temperature of from cooling temperature to elevated temperature, preferably 0° to 100° C.

The base used in the above reactions includes any conventional bases, preferably tri(lower alkyl)amines, N-lower alkylmorpholines, N,N-di(lower alkyl)anilines, pyridine, alkali metal hydrogen carbonates, alkali metal carbonates, and the like.

The solvent used in the above reactions includes any conventional inert solvents, preferably acetone, toluene tetrahydrofuran, dioxane, methylene chloride, chloroform, dimethylformamide, dimethyl sulfoxide, methanol, ethanol, and the like.

In case of $Z^1$ being two hydrogen atoms, the above reaction proceeds without racemization, and hence, when an optically active starting compound wherein $Z^1$ is two hydrogen atoms is used, there can be obtained an optically active compound [I].

Besides, the compounds [I] can optionally be subjected to optical resolution to give each optically active compounds [I]. The resolving agent may be any conventional resolving agents and further includes an optically active 3-[(5-chloro-2-nitrophenyl)thio]-2-hydroxy3-(4-methoxyphenyl)propionic acid. For instance, an optically active compound [I] can be obtained by reacting a racemic compound [I] with a resolving agent to form a diastereomer salt, dividing the salt into each isomer by the difference of solubility in a solvent, followed by treating With a basic substance.

The desired compounds [I] of this invention may be used in a free form or in the form of a pharmaceutically acceptable salt. The pharmaceutically acceptable salt includes inorganic acid salts [e.g. hydrochloride, hydrobromide, sulfate, etc.), or organic acid addition salts (e.g. oxalate, fumarate, maleate, etc.).

The compounds [I] of this invention include also the optical isomers owing to the asymmetric carbon at 2-position of the thiazine or oxazine ring and also a mixture of the isomers.

The compounds [I] or pharmaceutically acceptable salts thereof of this invention can be administered orally or parenterally to a warm-blooded animal, including human being, and can be used in a conventional pharmaceutical preparation, such as tablets, granules, capsules, powders, injections, and the like.

The dosage of the compounds [I] or pharmaceutically acceptable salts thereof of this invention may vary depending on the administration route, age, weight and state of patient, severity of diseases, and the like, but is usually in a range of about 0.1 to 100 mg/kg per day, preferably about 3 to 30 mg/kg per day.

The starting compounds [II] include novel compounds of the formula:

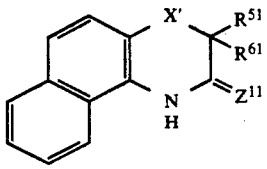

[II-a]

wherein X' is sulfur atom or oxygen atom; $R^{51}$ and $R^{61}$ are the same or different and are each i) hydrogen atom, ii) a lower alkyl, iii) a cycloalkyl, iv) a substituted phenyl, v) naphthyl, vi) a lower alkyl which is substituted by a substituted or unsubstituted phenyl, or vii) a sulfur-containing monoheterocyclic group; $Z^{11}$ is oxygen atom or two hydrogen atoms; provided that when $Z^{11}$ is two hydrogen atoms and $R^{51}$ and $R^{61}$ are both hydrogen atom, X' is sulfur atom, which can be prepared by the following processes.

The compounds [II-a] wherein $Z^{11}$ is oxygen atom can be prepared by reacting a compound of the formula:

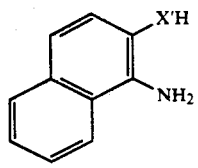

[X]

wherein X' is as defined above, with a compound of the formula:

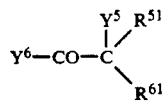

[XI]

wherein $Y^5$ is a halogen atom, $Y^6$ is a halogen atom or a lower alkoxy, and $R^{51}$ and $R^{61}$ are as defined above, in the presence or absence of a base (e.g. sodium acetate, potassium hydroxide, etc.), and when a compound of the formula:

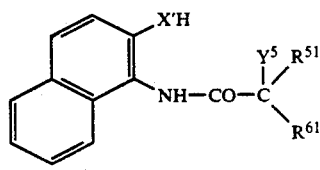

[XII]

wherein $R^{51}$, $R^{61}$, X', and $Y^5$ are as defined above, is obtained, and the above compound [XII] is further subjected to a ring-closing reaction in the presence of a base (e.g. potassium carbonate, etc.).

The compounds [II-a] wherein $Z^{11}$ is oxygen atom, and one of $R^{51}$ and $R^{61}$ is hydrogen atom and other is a substituted phenyl, naphthyl, a lower alkyl which is substituted by a substituted or unsubstituted phenyl or a sulfur-containing monoheterocyclic group can be prepared by halogenating a compound of the formula:

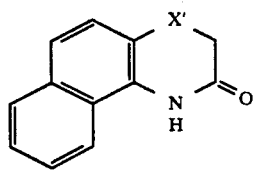

[XIII]

wherein X' is as defined above, then reacting the resulting 3-halogenated compound with a compound selected from a substituted benzene, naphthalene and a sulfur-containing monoheterocyclic compound in the presence of a Lewis acid (e.g. stannic chloride, etc.), or reacting the compound [XIII] with a substituted or unsubstituted benzaldehyde compound in the presence of a base (e.g. sodium methoxide, etc.), followed by subjecting to catalytic reduction with a catalyst (e.g. palladium on charcoal, etc.).

Besides, the compounds [II-a] wherein $Z^{11}$ is two hydrogen atoms can be prepared by reducing the corresponding compounds [II-a] wherein $Z^{11}$ is oxygen atom in the presence of a reducing agent (e.g. alkali metal borohydride, diborane, etc.).

Another starting compounds [II] can also be prepared from a corresponding substituted or unsubstituted 2-amino(thio)phenol or a corresponding substituted or unsubstituted 1-amino-2-naphthol (or naphthalenethiol) in accordance with the procedure desclosed above.

[ACTIVITIES]

The activities of the compounds of this invention were tested.

Experiment 1

Activity against entrance of calcium into cerebral synaptosome:

A cerebral synaptosome suspension was prepared from the cerebral cortex of rat in accordance with the procedure disclosed in The Journal of Physiology, 1989, 387, pages 415–423. To the suspension were added a fluorescent reagent (cf. "Note" hereinbelow) and a solution of test drug, and thereto was further added potassium chloride to depolarize. The fluorescent strength of the mixture was measured at 500 nm when irradiating mutually UV rays of wavelength of 340 nm and 380 nm with an apparatus for measuring intracellular calcium (CAF-100, manufactured by Nippon Bunko K.K.). The activity of the test drug for inhibiting the entrance of calcium into the synaptosome was calculated based on the rate of specific change ($\Delta R$) of fluorescent strength at peak by the following equation. As a control, dimethylsulfoxide was used instead of the test drug.

Inhibitory rate of calcium entrance (%) =

$$\left[ 1 - \frac{\text{Average } [\Delta R] \text{ in medicated group}}{\text{Average } [\Delta R] \text{ in control group}} \right] \times 100$$

wherein R=fluorescent strength at 340 nm/fluorescent strength at 380 nm.

[Note]:The fluorescent reagent=1-(2-(5'-carboxyoxazol-2'-yl]-6-aminobenzofuran-5-oxy)-2-(2'-amino-5'-methylphenoxy)ethane-N,N,N',N'-tetraacetic acid pentaacetoxymethyl ester (tradename, Fura 2-MA, manufactured by Dojin Kenkyusho).

Results

When the compounds as shown in the following Table 1 were used as the test drug in a concentration of $10^{-5}$M, these compounds showed the inhibitory activity of calcium entrance as shown in Table 1.

TABLE 1

Test compound:

[Structure: benzothiazine-type core with substituents $R^1$, $R^2$ on benzene ring; $R^5$ on carbon bearing H; $Z^1$, $Z^2$ on positions; linker -C(=Z^2)-A-N(R^7)(R^8)]

| No. | $R^1$ | $R^2$ | $R^5$ | $Z^1$ | $Z^2$ | A | $-NR^7R^8$ | Inhibitory rate of calcium entrace (%) |
|---|---|---|---|---|---|---|---|---|
| 1 | (2-methylphenyl: R¹=CH₃, R²=H on ortho-substituted benzene) | | 4-Cl-phenyl | $H_2$ | O | $-CH_2-$ | $-N(CH_3)_2$ | 69.8 |
| 2 | (2-methylphenyl) | | 4-Cl-phenyl | $H_2$ | O | $-CH_2-$ | $-N(C_2H_5)_2$ | 54.2 |
| 3 | (2-methylphenyl) | | 3-CF₃-phenyl | O | $H_2$ | $-CH_2CH_2-$ | $-N(CH_3)_2$ | 59.6 |
| 4 | (2-methylphenyl) | | 4-Cl-phenyl | O | $H_2$ | $-CH_2CH_2-$ | $-N(CH_3)(CH_2CH=CH_2)$ | 67.0 |
| 5 | H | H | 4-Cl-phenyl | $H_2$ | O | $-CH_2-$ | $-N(CH_3)(CH_2CH_2\text{-3,4-dimethoxyphenyl})$ | 70.1 |
| 6 | (2-methylphenyl) | | 4-Cl-phenyl | $H_2$ | O | $-CH_2-$ | piperidino | 55.6 |

Test compound:

[Structure: same core, different $Z^1/Z^2$ arrangement]

| No. | $R^1$ | $R^2$ | $R^5$ | $Z^1$ | $Z^2$ | A | $-NR^7R^8$ | Inhibitory rate of calcium entrace (%) |
|---|---|---|---|---|---|---|---|---|
| 7 | (2-methylphenyl) | | 3-Cl-phenyl | $H_2$ | O | $-CH_2-$ | $-N(C_2H_5)_2$ | 54.2 |

TABLE 1-continued

| | | | | | | | | |
|---|---|---|---|---|---|---|---|---|
| 8 |  |  | $H_2$ | O | $-CH_2-$ | $-N\begin{smallmatrix}CH_3\\CH_3\end{smallmatrix}$ | | 56.2 |
| 9 | 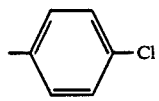 |  | O | $H_2$ | $-CH_2CH_2-$ | $-N\overset{\frown}{\phantom{N}}N$ | | 51.8 |
| 10 | 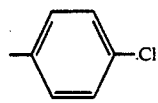 |  | O | $H_2$ | $-CH_2CH_2-$ | $-N\begin{smallmatrix}CH_3\\CH_3\end{smallmatrix}$ | | 53.4 |

Experiment 2

Activity for protecting cerebral anoxia induced by potassium cyanide:

The test drug was orally administered to mice. One hour after the administration, potassium cyanide (2.4 mg/kg) was administered into the tail vein, and the survival time (second) of the mice was measured. On the basis of the average survival time in the medicated group and the control group, the rate of prolonging of the survival time was calculated by the following equation. In the control group, distilled water was administered instead of the test drug.

Rate of prolonging of survival time (%) =

$$\left[\frac{\text{Average survival time in medicated group}}{\text{Average survival time in control group}} - 1\right] \times 100$$

Results

When the compounds as shown in the following Table 2 were orally administered as the test drug in a dose of 10 mg/kg, these compounds showed the prolonging rate of survival time as shown in Tables 2A and 2B.

TABLE 2A

Test compound:

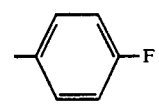

| No. | $R^1$ | $R^2$ | $R^5$ | $Z^1$ | $Z^2$ | A | $R^7$ | $R^8$ | Prolonging rate of survival time (%) |
|---|---|---|---|---|---|---|---|---|---|
| 1 | H | H | —⟨⟩—Cl | $H_2$ | O | $-CH_2-$ | $-C_2H_5$ | $-C_2H_5$ | 62 |
| 2 | ⟨⟩ (o-tolyl) | | —⟨⟩—Cl | $H_2$ | O | $-CH_2-$ | $-CH_3$ | $-CH_3$ | 49 |
| 3 | ⟨⟩ (o-tolyl) | | —⟨⟩—Cl | $H_2$ | O | $-CH_2-$ | $-C_2H_5$ | $-C_2H_5$ | 65 |
| 4 | ⟨⟩ (o-tolyl) | | —⟨⟩—F | O | $H_2$ | $-CH_2-$ | $-CH_3$ | $-CH_3$ | 62 |

TABLE 2A-continued

Test compound: [structure with R¹, R², R⁵, Z¹, Z², A, R⁷, R⁸ substituents on benzothiazine-type skeleton]

| No. | R¹ | R² | R⁵ | Z¹ | Z² | A | R⁷ | R⁸ | Prolonging rate of survival time (%) |
|---|---|---|---|---|---|---|---|---|---|
| 5 | (2-methylphenyl) | | (4-fluorophenyl) | O | H₂ | —CH₂CH₂— | —CH₃ | —CH₃ | 56 |
| 6 | H | H | (thiophene) | H₂ | O | —CH₂— | —C₂H₅ | —C₂H₅ | 48 |

TABLE 2B

Test compound: [naphtho-fused structure with X, R⁵, R⁶, R⁷, R⁸ substituents]

| No. | X | R⁵ | R⁶ | R⁷ | R⁸ | Prolonging rate of survival time (%) |
|---|---|---|---|---|---|---|
| 7 | S | —CH₃ | —CH₃ | —C₂H₅ | —C₂H₅ | 42 |
| 8 | O | —H | —H | —CH₃ | —CH₃ | 93 |

The compounds (I) of this invention can inhibit the calcium entrance into the cerebral synaptosome and show excellent central calcium antagonistic activity and/or excellent calcium antagonistic activity in cerebral blood vessel, and can be used for the treatment and prophylaxis of cerebral diseases due to cerebral blood flow disorder at acute and chronic periods, for example, subarachnoid hemorrhage, cerebral infarction, etc. The compounds (I) of this invention have also an activity for protecting cerebral neurocyte. For example, when 2-(4-chlorophenyl)-4-(diethylamino)acetyl-3,4-dihydro-2H-1,4-benzothiazine was intraperitoneally administered to evanescent cerebral ischemic rats with ligating four vessels in a dose of 1.5 mg/kg twice a day for four days, it increased the number of normal pyramidal cells at hippocampul CA₁ region in about 90% in comparison with the non-medicated group. Accordingly, the compounds (I) of this invention can effectively be used for the prophylaxis, treatment and amelioration of sequelae of cerebral neurocyte dyscrasia, for example, disturbances of consciousness (e.g. somnolenz, sopor, coma, stupor, clouding of consciousness, etc.), motor paralysis (e.g. parkinsonism, etc.), cerebral neuropathy (e.g. dysuria, etc.), speech and language disorders (e.g. articulation disorders, aphasia, semantic aphasia, etc.), sensitive disorders (e.g. pain, sysesthesia, heat sensibility disorder, etc.), psychological disorders (e.g. dementia, hallucination, delusion, delirium, poriomania, melancholia, neurosis, emotional incontinence, etc.), and the like, and further the prophylaxis of palindromia and also the prophylaxis of exacerbation and progression of the symptoms. Moreover, the compounds (I) of this invention show little activity to heart and circular organs and hence has characteristics of direct action onto the cerebral cells. In addition, the compounds (I) of this invention have low toxicity and has high safety. For example, when the compounds of this invention such as 2-(4-chlorophenyl)-4-(diethylamino)acetyl-3,4-dihydro-2H-1,4-benzothiazine oxalate, 3-(4-chlorophenyl)-1-(diethylamino)acetyl-2,3-dihydro-1H-naphtho[2,1-b][1,4]thiazine oxalate, and 1-[3-(dimethylamino)-propyl]-3-(3-trifluoromethylphenyl)-1H-naphtho[2,1-b][1,4]thaizin-2[3H]-one oxalate were orally administered to mice in a dose of 500 mg/kg, no mouse died even after 7 days.

EXAMPLES

The compounds of this invention is illustrated by the following Examples but should not be construed to be limited thereto.

EXAMPLE 1

(1) To a mixture of 2-(4-fluorophenyl)-3-oxo-3,4-dihydro-2H-1,4-benzothiazine (4.0 g), sodium borohydride (2.91 g) and tetrahydrofuran (100 ml) is added dropwise with stirring boron trifluoride etherate complex (12. 5 ml) at room temperature, and the mixture is refluxed for 1.5 hour. After cooling, to the mixture is added dropwise 10% hydrochloric acid (35 ml), and the mixture is further refluxed for one hour. The reaction mixture is poured into ice water and made alkaline with potassium carbonate and extracted with ethyl acetate. The ethyl acetate layer is washed, dried and distilled to remove the solvent. The residue is recrystallized from isopropyl ether to give 2-(4-fluorophenyl)-3,4-dihydro-2H-1,4-benzothiazine (3.45 g, yield 91%) as crystals.

M.p. 134°–135.5° C.

(2) To a solution of the compound obtained above (2.60 g) and triethylamine (3.6 ml) in methylene chloride (45 ml) is added dropwise a solution of chloroacetyl chloride (1.70 ml) in methylene chloride (5 ml) under ice cooling, and the mixture is stirred at room temperature for one hour. After the solvent is distilled off, to the residue are added ethyl acetate and water, and the ethyl acetate layer is washed with water, dried and distilled to remove the solvent. The residue is recrystallized from isoporpyl ether to give 4-chloroacetyl2-(4-fluorophenyl)-3,4-dihyro-2H-1,4-benzothiazine (3.02 g, yield 89%).

M.p. 122°–123.5° C.

(3) To a solution of the compound obtained above 1.20 g) in tetrahydrofuran (15 ml) is added a 15% solution of dimethylamine in methanol (15 ml), and the mixture is stirred at room temperature for 20 hours. The solvent is distilled off, and to the residue are added ethyl acetate and aqueous sodium hyrogen carbonate solution. The ethyl acetate layer is washed, dried, and distilled to remove the solvent. The residue is dissolved in ethanol-ether and thereto is added one equivalent of oxalic acid. The resulting precipitate is recrystallized from ethanol-ether to give 4-(dimethylamino)acetyl-2-(4-fluorophenyl)-3,4-dihydro-2H-1,4-benzothiazine oxalate (1.45 g, yield 93%).

M.p. 171.5°-172.5° C.

EXAMPLES 2 to 17

(1) The corresponding starting materials are treated in the same manner as described in Example 1-(1) to give the compounds as shown in Tables 3 and 4.

TABLE 3

| Compd. symbol | $R^2$ | $R^3$ | X | M.p. (solvent for recrystal.) |
|---|---|---|---|---|
| A | H | Cl | S | 139–142° C. (isopropyl ether) |
| B | H | H | O | 99–100° C. (isopropyl ether-n-hexane) |

TABLE 4

| Compd. symbol | $R^5$ | M.p. (solvent for recrystal.) etc. |
|---|---|---|
| C | 3-CF$_3$-phenyl | 74–75° C. (n-hexane) |
| D | 1-naphthyl | 101.5–103° C. (isopropyl ether-n-hexane) |
| E | 2-thienyl | 84–89° C. (ethyl acetate-n-hexane) |
| F | 2,4-dichlorophenyl | 93–95° C. (ethyl acetate-n-hexane) |
| G | 4-methylphenyl | 110–112° C. (ethyl acetate-n-hexane) |

(2) The compounds obtained in the above (1) or corresponding compounds are reacted with chloroacetyl chloride in the same manner as described in Example 1-(2) to give the compounds as shown in Tables 5 and 6.

TABLE 5

| Compd. symbol | $R^2$ | $R^3$ | X | M.p. (solvent for recrystal.) etc. |
|---|---|---|---|---|
| A | H | Cl | S | 119.5–121° C. (ethyl acetate-n-hexane) |
| B | H | H | O | caramel, |

TABLE 5-continued

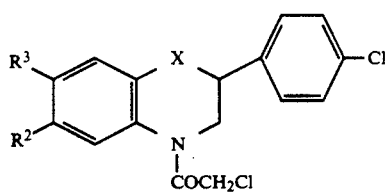

| Compd. symbol | R² | R³ | X | M.p. (solvent for recrystal.) etc. |
|---|---|---|---|---|
| | | | | MS (m/z): 321 (M+),<br>IR $\nu_{max}^{Neat}$(cm⁻¹): 1670 |

TABLE 6

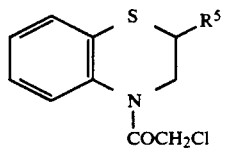

| Compd. symbol | R⁵ | M.p. (solvent for recrystal.) etc. |
|---|---|---|
| C | 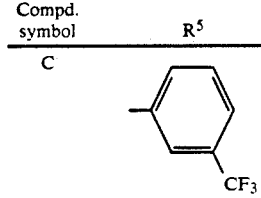 | 104–105.5° C.<br>(ethyl acetate-n-hexane) |
| D | 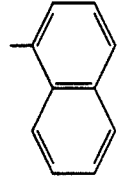 | 133–135.5° C. (ethanol) |
| E | 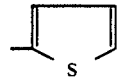 | 93–97° C. (ethanol) |
| F | 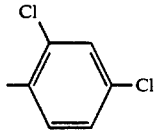 | caramel, MS (m/z): 371 (M+),<br>IR $\nu_{max}^{CHCl_3}$(cm⁻¹): 1670 |

TABLE 6-continued

| Compd. symbol | R⁵ | M.p. (solvent for recrystal.) etc. |
|---|---|---|
| G | ―〈 〉―CH₃ | 121–123° C. (isopropyl ether) |
| H | ―〈 〉―Cl | 94–95° C. (ethanol) |
| I | ―〈 〉―OCH₃ | 110–112° C. (ether) |

(3) The compounds of the above (2) or the compound in Example 1-(2) are reacted with the corresponding amine compound in the same manner as described in Example 1-(3) to give the compounds as shown in Table 7 to 9.

TABLE 7

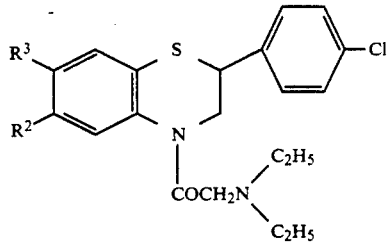

| Ex. No. | R² | R³ | M.p. (solvent for recrystal.) |
|---|---|---|---|
| 2 | H | Cl | Oxalate: 162–163.5° C. (ethanol-ether) |

TABLE 8

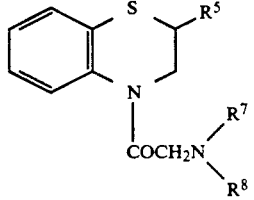

| Ex. No. | R⁵ | N(R⁷)(R⁸) | M.p. (solvent for recrystal.) etc. |
|---|---|---|---|
| 3 | 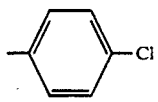 | N(C₂H₅)₂ | 65–68° C. (isopropyl ether-n-hexane)<br>oxalate:<br>143–144° C. (dec.) (methanol-ether) |

TABLE 8-continued

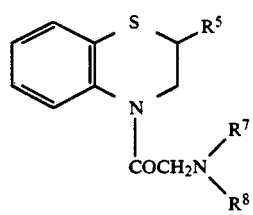

| Ex. No. | R⁵ | NR⁷R⁸ | M.p. (solvent for recrystal.) etc. |
|---|---|---|---|
| 4 | 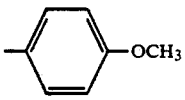 (–C₆H₄–OCH₃, para) | N(C₂H₅)₂ | oxalate: 180–182° C. (ethanol) |
| 5 | 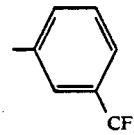 (–C₆H₄–CF₃, meta) | N(C₂H₅)₂ | oxalate: 111–113° C. (dec.) (ethanol-ether) |
| 6 | 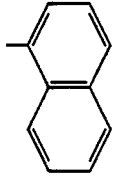 (1-naphthyl) | N(C₂H₅)₂ | oxalate: 146–148° C. (dec.) (ethanol-ether) |
| 7 |  (2-thienyl) | N(C₂H₅)₂ | oxalate: 166.5–167.5° C. (dec.) (ethanol-ether) |
| 8 | 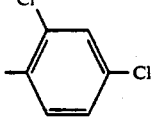 (2,4-dichlorophenyl) | N(CH₃)₂ | oxalate: 192–194° C. (dec.) (ethanol-ether) |
| 9 | 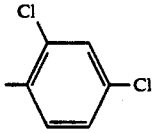 (2,4-dichlorophenyl) | N(C₂H₅)₂ | oxalate: 177–179° C. (ethanol-ether) |
| 10 | 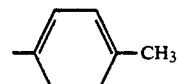 (–C₆H₄–CH₃, para) | N(C₂H₅)₂ | oxalate: 161–163° C. (ethanol-ether) |

TABLE 9

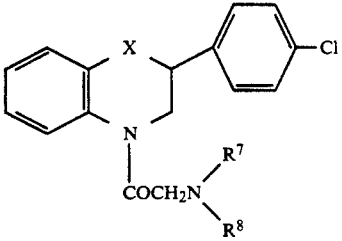

| Ex. No. | X | R⁷ N R⁸ | M.p. (solvent for recrystal.) etc. |
|---|---|---|---|
| 11 | S | N(CH₃)₂ | hydrochloride: 253.5–255.5° C. (dec.) (ethanol-ether) |
| 12 | S |  | oxalate: 177–179° C. (dec.) (ethanol-ether) |
| 13 | S |  | oxalate: 197.5–198.5° C. (dec.) (methanol) |
| 14 | O | N(CH₃)₂ | oxalate: 211–213° C. (dec.) (methanol-ether) |
| 15 | O | N(C₂H₅)₂ | oxalate: 144–146° C. (dec.) (ethanol-ether) |
| 16 | S | NHCH₃ | oxalate: 225–227° C. (dec.) (methanol) |
| 17 | S |  | oxalate: powder MS (m/z): 498, 496 (M⁺), 345 IR ν$_{max}^{Nujol}$(cm⁻¹): 1720, 1670 |

EXAMPLE 18

(1) To a mixture of 2-(4-chlorophenyl)-3,4-dihydro-2H-1,4-benzothiazine (9.62 g), sodium hydrogen carbonate (6.0 g), methylene chloride (100 ml) and water (50 ml) is added dropwise with stirring a solution of acryloyl chloride (5.0 g) in methylene chloride (20 ml) under ice cooling over a period of about 30 minutes. The mixture is stirred at room temperature for 3 hours, and the organic layer is washed and dried. After the solvent is distilled off, the resulting crystals are washed with n-hexane to give 2-(4-chlorophenyl)-4-acryloyl-3,4-dihyro-2H-1,4-benzothiazine (10.76 g, yield 93%).

M.p. 122°–124° C.

(2) To a suspension of the compound obtained above (2.21 g) in ethanol (50 ml) is added a 31% solution of dimethylamine in ethanol (20 ml), and the mixture is stirred at room temperature for one hour. The solvent is distilled off, and to the residue is added hydrogen chloride-ethanol. Ethanol is distilled off, and the residue is recrystallized from ethanol-ether to give 2-(4-chlorophenyl)-4-[3-(dimethylamino)propionyl]-3,4-dihydro-2H-1,4-benzothiazine hydrochloride (2.13 g, yield 77%).

M.p. 188°–190° C.

EXAMPLE 19

The corresponding starting material is treated in the same manner as described in Example 18-(2) to give the compound as shown in Table 10.

TABLE 10

| Ex. No. | R⁷ N R⁸ | M.p. (solvent for recrystal.) |
|---|---|---|
| 19 | N(C₂H₅)₂ | hydrochloride: 191–194° C. (ethanol-ether) |

EXAMPLE 20

To a solution of 2-(4-chlorophenyl)-3,4-dihydro-2H-1,4-benzothiazine (0.52 g) and N,N-dimethylaniline (0.97 g) in methylene chloride (15 ml) is added dimethylaminoacetyl chloride hydrochloride (0.63 g) under ice cooling, and the mixture is stirred at the same temperature for 2.5 hours. To the reaction mixture is added aqueous sodium hydrogen carbonate solution, and is extracted with chloroform. The chloroform layer is washed, dried and distilled to remove the solvent. The residue is treated with hydrochloric acid and the resulting salt is recrystallized from ethanol-ether to give 2-(4-chlorophenyl)-4-(dimethylamino)acetyl-3,4-dihydro-2H-1,4-benzothiazine hydrochloride (0.63 g, yield 86%).

M.p. 253°-255° C. (dec.)

EXAMPLE 21

A mixture of 2-(4-chlorophenyl)-4-(N-methylaminoacetyl)-3,4-dihydro-2H-1,4-benzothiazine (1.80 g), allyl bromide (0.52 ml), potassium carbonate (2.25 g) and dimethylformamide (20 ml) is stirred at room temperature for 3.5 hours. The reaction mixture is poured into water, and the mixture is extracted with ethyl acetate. After the solvent is distilled off, the residue is purified by silica gel column chromatography (solvent, chloroform:methanol=40:1). The caramel thus obtained is dissolved in ether and thereto is added 1.1 equivalent of oxalic acid. The resulting precipitate is washed with ether and dried to give 4-(N-allyl-N-methylaminoacetyl)-2-(4-chlorophenyl)-3,4-dihydro-2H-1,4-benzothiazine oxalate as powder.

Mass (m/z):374, 372 (M+)

IR $\gamma_{max}^{Nujol}$ (cm$^{-1}$): 1720, 1680

EXAMPLE 22

2-(4-Chlorophenyl)-4-(N-methylaminoacetyl)-3,4-dihyro-2H-1,4-benzothiazine and 2-propynyl bromide are treated in the same manner as described in Example 21 to give 4-[N-(2-propynyl)-N-methylaminoacetyl]-2-(4-chlorophenyl)- 3,4-dihydro-2H-1,4-benzothiazine oxalate.

M.p. 169.5°-171° C. (dec.) (recrystallized from ethanol-ether).

EXAMPLE 23

(1) To a mixture of 2-(4-chlorophenyl)-3,4-dihydro2H-1,4-benzothiazine (1.08 g), ethyl acetate (20 ml) and aqueous sodium hydrogen carbonate solution (20 ml) is added dropwise a solution of 4-bromobutyryl chloride (0.97 g) in ethyl acetate (5 ml) with stirring under ice cooling. The ethyl acetate layer is washed, dried and distilled to remove the solvent. The residue is recrystallized from ethyl acetate-n-hexane to give 4-(4-bromobutyryl)-2-(4-chlorophenyl)-3,4-dihyro-2H-1,4-benzothiazine (1.58 g, yield 93%).

M.p. 91°-92° C.

(2) To a solution of the compound obtained above (1.19 g) in tetrahydrofuran (5 ml) is added a 20% solution of dimethylamine in tetrahydrofuran (5 ml), and the mixture is stirred at room temperature for 5 hours. After the reaction is completed, the solvent is distilled off, and to the residue are added ethyl acetate and aqueous sodium hydrogen carbonate solution. The ethyl acetate layer is washed, dried, and distilled to remove the solvent. The oily residue is dissolved in ethanol and thereto is added oxalic acid (0.22 g). The resulting precipitate is recrystallized from ethanol-ether to give 2-(4-chlorophenyl)-4-[4-(dimethylamino)butanoyl]-3,4-dihydro-2H-1,4-benzothiazine oxalate (1.03 g, yield 76%).

M.p. 170°-170.5° C. (dec.)

EXAMPLE 24

To a solution of 1-amino-2-naphthalenethiol (27.81 g) in ethanol (500 ml) is added sodium borohydride (11.35 g) at room temperature. The mixture is stirred for 20 minutes, and thereto is added dropwise acetic acid (200 ml) and is further added sodium acetate (24.6 g). To the mixture is further added dropwise methyl α-bromo-4-chlorophenylacetate (46.8 g), and the mixture is sitrred at room temperature under argon overnight. The reaction mixture is poured into ice water and the resulting precipitate is separated by filtration, washed, dried and recrystallized from tetrahydrofuran-n-hexane to give 3-(4-chlorophenyl)-1H-naphtho-[2,1-b][1,4]thiazin-2(3H)-one (44.45 g, yield 82.6%) as crystals.

M.p. 235.5°-237.5° C.

EXAMPLES 25 to 31

The corresponding starting materials are treated in the same manner as described in Example 24 to give the compounds as shown in Table 11.

TABLE 11

| Ex. No. | R⁵ | R⁶ | M.p. (°C.) |
|---|---|---|---|
| 25A | H | H | 200-201° C.*1 |
| 25B | CH₃ | CH₃ | 182-183° C.*2 |
| 26 | H | 3-Cl-C₆H₄ | 192-194° C.*1 |
| 27 | H | 2-Cl-C₆H₄ | 250-252.5° C.*1 |
| 28 | H | 4-Br-C₆H₄ | 244-246° C.*1 |
| 29 | H | 4-F-C₆H₄ | 251-253° C.*1 |
| 30 | H | 3-CF₃-C₆H₄ | 203.5-206° C.*1 |

TABLE 11-continued

[Structure: naphtho-thiazine with R5, R6, S, N-H, C=O]

| Ex. No. | R⁵ | R⁶ | M.p. (°C.) |
|---------|----|----|-----------|
| 31 | H | 2,4-dichlorophenyl | 233–235° C.*1 |

*1 Recrystallized from tetrahydrofuran-hexane
*2 Recrystallized from tetrahydrofuran-isopropyl ether

EXAMPLE 32

To a mixture of 1-amino-2-naphthol (9.4 g), N,N-dimethylaniline (17.87 g) and tetrahydrofuran (160 ml) is added dropwise α-bromo-4-chlorophenylacetyl chloride (18.97 g) under ice cooling, and the mixture is stirred for one hour. To the reaction mixture is added ethyl acetate, and the ethyl acetate layer is washed, dried and distilled to remove the solvent. The resulting oil is dissolved in acetone (500 ml) and thereto is added potassium carbonate (40.8 g), and the mixture is refluxed for 2 hours, and acetone is distilled off. To the residue is added water, and the precipitate is separated by filtration, washed, dried and recrystallized from tetrahyrofuran to give 3-(4-chlorophenyl)-1H-naphtho[2,1-b][1,4]oxazin-2(3H)-one (13.29 g, yield 72.8%).
M.p. 230.5°–232° C.

EXAMPLE 33

1-Amino-2-naphthol and bromoacetyl chloride are reacted in the same manner as described in Example 32 to give 1H-naphtho[2,1-b][1,4]oxazin-2(3H)-one.
M.p. 219°–220.5° C. (recrystallized from tetrahydrofuran)

EXAMPLE 34

To a solution of 3-(4-chlorophenyl)-1H-naphtho[2,1-b][1,4]thiazin-2(3H)-one (38.45 g) and sodium borohydride (22.32 g) in tetrahydrofuran (1.0 liter) is added dropwise with stirring boron trifluoride etherate complex (100 ml) at room temperature, and the mixture is refluxed for 2 hours. After cooling, to the mixture are added methanol (200 ml), 10% hydrochloric acid (300 ml) and conc. hydrochloric acid (150 ml) in this order and the mixture is further refluxed for 4 hours. To the reaction mixture is added ice water and the mixture is made alkaline with potassium carbonate and extracted with ethyl acetate. The ethyl acetate layer is washed, dried and distilled to remove the solvent. The residue is recrystallized from tetrahydrofuran-n-hexane to give 3-(4-chlorophenyl)-2,3-dihydro-1H-naphtho[2,1-b][1,4]thiazine (32.3 g, yield 88%) as crystals.
M.p. 185°–186.5° C.

EXAMPLES 35 to 44

The compounds obtained in Examples 25 to 33 are treated in the same manner as described in Example 34 to give the compounds as shown in Table 12.

TABLE 12

[Structure: naphtho fused with X, R5, R6, N-H ring]

| Ex. No. | X | R⁵ | R⁶ | M.p. (°C.) |
|---------|---|----|----|-----------|
| 35 | S | H | H | 102–104° C.*2 |
| 36 | S | CH₃ | CH₃ | 125–128° C.*2 |
| 37 | S | H | 3-chlorophenyl | 135.5–136.5° C.*2 |
| 38 | S | H | 2-chlorophenyl | 159–160.5° C.*2 |
| 39 | S | H | 4-bromophenyl | 203–206° C.*2 |
| 40A | S | H | 4-fluorophenyl | 174–176° C.*2 |
| 40B | S | H | 4-methylphenyl | 180–182° C.*2 |
| 41 | S | H | 3-trifluoromethylphenyl | 137–139° C.*2 |
| 42 | S | H | 2,4-dichlorophenyl | 156–158° C.*2 |
| 43 | O | H | 4-chlorophenyl | 168–170° C.*1 |
| 44 | O | H | H | hydrochloride: 211–214° C.*3 |

*1 Recrystallized from tetrahydrofuran-hexane
*2 Recrystallized from ethyl acetate-n-hexane
*3 Recrystallized from ethanol
[Note]: The compound of Example 44 is disclosed in Journal of the Chemical Society Vol. 121, page 647.

EXAMPLE 45

(1) To a suspension of 3-(4-chlorophenyl)-2,3-dihydro-1H-naphtho[2,1-b][1,4]thiazine (14.09 g) and triethylamine (13.7 g) in methylene chloride (300 ml) is added dropwise chloroacetyl chloride (10.2 g) under ice cooling. After the mixture is stirred at room temperature for one hour, the reaction mixture is washed, dried and distilled off to remove the solvent. The residue is crystallized from isopropyl ether to give 1-chloroacetyl-3-(4-chlorophenyl)-2,3-dihyro-1H-naphtho[2,1-b][1,4]thiazine (15.45 g, yield 88%).

M.p. 172°–174° C.

(2) To a suspension of the compound obtained above (15.45 g) and sodium iodide (13.6 g) in tetrahydrofuran (100 ml) is added diethylamine (80 ml). After the mixture is stirred at room temperature for 2 hours, the solvent and diethylamine are distilled off, and to the residue are added ethyl acetate and aqueous sodium hydrogen carbonate solution. The ethyl acetate layer is washed, dried, and concentrated to give 3-(4-chlorophenyl)-1-(diethylamino)acetyl-2,3-dihydro-1H-naphtho[2,1-b][1,4]thiazine (17.0 g) as an oil. The product is dissolved in ethanol and thereto is added one equivalent of fumaric acid. The resulting precipitate is recrystallized from 1 % aqueous acetone to give 3-(4-chlorophenyl)-1-(diethylamino)acetyl-2,3-dihydro-1H-naphtho[2,1-b][1,4]-thiazine fumarate (17.45 g, yield 81%).

M.p. 164.5°–166° C.

EXAMPLES 46 to 54

(1) The compounds obtained in Examples 35 to 44 are reacted with chloroacetyl chloride in the same manner as described in Example 45-(1) to give the compounds as shown in Table 13.

TABLE 13

| Ex. No. | X | R⁵ | R⁶ | Physical properties, etc. |
|---|---|---|---|---|
| 46(1) | S | CH₃ | CH₃ | caramel: Mass (m/z): 305 (M⁺) IR $\nu_{max}^{Neat}$(cm⁻¹): 1675 |
| 47(1) | S | H | 3-Cl-C₆H₄- | m.p. 156–157.5° C.*2 |
| 48(1) | S | H | 2-Cl-C₆H₄- | m.p. 139–141° C.*3 |
| 49(1) | S | H | 4-Br-C₆H₄- | m.p. 178–180° C.*4 |
| 50(1) | S | H | 4-F-C₆H₄- | m.p. 125–127° C.*4 |

TABLE 13-continued

| Ex. No. | X | R⁵ | R⁶ | Physical properties, etc. |
|---|---|---|---|---|
| 51(1) | S | H | 3-CF₃-C₆H₄- | m.p. 143–145° C.*4 |
| 52(1) | S | H | 2,4-diCl-C₆H₃- | m.p. 123–125° C.*4 |
| 53(1) | O | H | 4-Cl-C₆H₄- | m.p. 132–134° C.*3 |
| 54(1) | O | H | H | oil: Mass (m/z): 261 (M⁺), IR $\nu_{max}^{Neat}$(cm⁻¹): 1675 |

*2 Recrystallized from ethyl acetate-n-hexane
*3 Recrystallized from ethanol
*4 Recrystallized from isopropyl ether (2) The products obtained in the above (1) are reacted with the corresponding amine compounds in the same manner as described in Example 45-(2) to give the compounds as shown in Tables 14 and 15.

TABLE 14

| Ex. No. | R⁵ | R⁶ | Physical properties, etc. |
|---|---|---|---|
| 46(2) | CH₃ | CH₃ | powder: Mass (m/z): 342 (M⁺) IR $\nu_{max}^{Nujol}$(cm⁻¹): 1720, 1675 |
| 47(2) | H | 3-Cl-C₆H₄- | m.p. 167–171.5° C. (dec.)*5 |
| 48(2) | H | 2-Cl-C₆H₄- | powder: Mass (m/z): 424 (M⁺) IR $\nu_{max}^{Nujol}$(cm⁻¹): 1720, 1680 |
| 49(2) | H | 4-Br-C₆H₄- | m.p. 182–184° C. (dec.)*5 |

TABLE 14-continued

Structure: naphthalene fused with S-CH(R⁵)(R⁶)-CH₂-N ring, N-COCH₂-N(C₂H₅)₂ · oxalate

| Ex. No. | R⁵ | R⁶ | Physical properties, etc. |
|---|---|---|---|
| 50(2) | H | 4-F-phenyl | m.p. 145–148° C.*5 |
| 51(2) | H | 3,5-diCl-phenyl | powder: Mass (m/z): 458 (M⁺)<br>IR $\nu_{max}^{Nujol}$(cm⁻¹): 1720, 1680 |
| 52(2) | H | 2,4-diCl-phenyl | powder: Mass (m/z): 458 (M⁺)<br>IR $\nu_{max}^{Nujol}$(cm⁻¹): 1720, 1680 |

*5 Recrystallized from ethanol-diethyl ether

TABLE 15

Structure: naphthalene fused with O-CH(R⁵)(R⁶)-CH₂-N ring, N-COCH₂-NR⁷R⁸

| Ex. No. | R⁵ | R⁶ | -N(R⁷)(R⁸) | Physical properties, etc. |
|---|---|---|---|---|
| 53(2) | H | 4-Cl-phenyl | N(C₂H₅)₂ | oxalate: m.p. 168–170° C. (dec.)*5 |
| 54(2) | H | H | N(CH₃)₂ | hydrochloride: m.p. 213–215° C. (dec.)*5 |

*5 Recrystallized from ethanol-diethyl ether

EXAMPLES 55 to 65

The products obtained in Examples 34, 35, 40A, 40B, 41 to 43 are reacted with the corresponding amine compounds in the same manner as described in Example 45 to give the compounds as shown in Table 16.

TABLE 16

Structure: naphthalene fused with X-CH(R⁵)-CH₂-N ring, N-COCH₂-NR⁷R⁸ · oxalate

| Ex. No. | X | R⁵ | -N(R⁷)(R⁸) | Physical properties, etc. |
|---|---|---|---|---|
| 55 | S | 4-Cl-phenyl | N(CH₃)₂ | m.p. 217–219° C. (dec.)*6 |
| 56 | S | 4-Cl-phenyl | pyrrolidinyl | m.p. 209–211° C. (dec.)*7 |
| 57 | S | 4-Cl-phenyl | piperidinyl | m.p. 234–236° C. (dec.)*7 |
| 58 | S | 4-Cl-phenyl | morpholinyl | m.p. 239–240° C. (dec.)*7 |

TABLE 16-continued

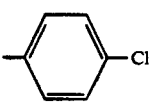

| Ex. No. | X | R⁵ | R⁷ / R⁸ (NR⁷R⁸) | Physical properties, etc. |
|---|---|---|---|---|
| 59 | S | 4-Cl-phenyl | NHCH₃ | m.p. 238.5–240.5° C. (dec.)*7 |
| 60 | S | H | N(CH₃)₂ | m.p. 215–216° C. (dec.)*6 |
| 61 | S | 4-F-phenyl | N(CH₃)₂ | m.p. 143–146° C.*5 |
| 62 | S | 4-CH₃-phenyl | N(CH₃)₂ | m.p. 215–217° C.*5 |
| 63 | S | 3-CF₃-phenyl | N(CH₃)₂ | m.p. 193–195° C. (dec.)*5 |
| 64 | S | 2,4-diCl-phenyl | N(CH₃)₂ | m.p. 151–153° C.*5 |
| 65 | O | 4-Cl-phenyl | N(CH₃)₂ | m.p. 226–228° C. (dec.)*7 |

*6 Recrystallized from methanol-diethyl ether
*7 Recrystallized from methanol

EXAMPLE 66

To a mixture of 3-(4-chlorophenyl)-2,3-dihydro-1H-naphtho[2,1-b][1,4]thiazine (0.62 g), N,N-dimethylaniline (2 ml) and methylene chloride (15 ml) is added in portions dimethylaminoacetyl chloride hydrochloride (1.26 g) under ice cooling. After the mixture is stirred at room temperature for 2 hours, to the reaction mixture is added aqueous sodium hydrogen carbonate solution, and the mixture is extracted with chloroform. The chloroform layer is washed, dried and distilled to remove the solvent. The residue is purified by silica gel column chromatography (CHCl₃ methanol=30:1) to give 3-(4-chlorophenyl)-1-(dimethylamino)acetyl-2,3-dihydro-1H-naphtho[2,1-b][1,4]thiazine (0.36 g, 45 %) as caramel.

The compound obtained above is dissolved in ether and thereto is added one equivalent of oxalic acid. The resulting precipitate is separated by filtration and is recrystallized from methanol-diethyl ether to give 3-(4-chlorophenyl)-1-(dimethylamino)acetyl-2,3-dihyro-1H-naphtho[2,1-b][1,4]-thiazine oxalate.

M.p. 216°–218° C. (dec.)

EXAMPLE 67

(1) To a mixture of 3-(4-chlorophenyl)-2,3-dihydro1H-naphtho[2,1-b][1,4]thiazine (1.50 g), sodium hydrogen carbonate (1.0 g), methylene chloride (30 ml) and water (15 ml) is added dropwise with stirring a solution of acryloyl chloride (0.90 g) in methylene chloride (10 ml) under ice cooling. The mixture is stirred at room temperature for 3 hours. The organic layer is separated, washed, dried and distilled to remove the solvent. The residue is chromatographed on silica gel (toluene : acetone =50 : 1) to give 3-(4-chlorophenyl)-1- propenoyl-2,3-dihydro-1H-naphtho[2,1-b][1,4]thiazine (1.37 g, 78 %) as powder.

Mass (m/z):365 (M+)
IR$\gamma_{max}^{Nujol}$(cm$^{-1}$):1660, 1620

(2) To a suspension of the compound obtained above (1.33 g) in tetrahydrofuran (10 ml) is added dropwise a 17 % solution of dimethylamine in methanol (15 ml). After the mixture is stirred at room temperature for one hour, the solvent is distilled off to give 3-(4-chlorophenyl)-1-[3-(dimethylamino)propionyl]-2,3-dihyro-1H-naphtho[2,1-b][1,4]-thiazine (1.39 g) as caramel.

The compound obtained above is dissolved in ether, and thereto is added one equivalent of oxalic acid. The resulting precipitate is separated by filtration and recrystallized from methanol to give 3-(4-chlorophenyl)-1-[3-(dimethylamino)propionyl]-2,3-dihydro-1H-naphtho[2,1-b][1,4]-thiazine oxalate.

M.p. 217°-219° C. (dec.)

EXAMPLES 69 to 70

The corresponding starting materials are treated in the same manner as described in Example 24 to give the compounds as shown in Table 17.

TABLE 17

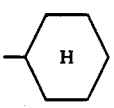

| Ex. No. | R$^5$ | R$^6$ | M.p. |
|---|---|---|---|
| 69 | CH$_3$ | H | 179.5-181° C.*$^1$ |
| 70 | ⬡-H | H | 215.5-217.5° C.*$^1$ |

*$^1$Recrystallized from tetrahydrofuran-n-hexane
*$^8$Recrystallized from tetrahydrofuran-diisopropyl ether

EXAMPLE 71

(1) A mixture of 1H-naphtho[2,1-b][1,4]thiazin-2(3H)-one (5.17 g), 4-chlorobenzaldehyde (5.62 g), sodium methoxide (1.73 g) and dimethylformamide (80 ml) is refluxed for 4.5 hours. After cooling, the reaction mixture is poured into water and the resulting precipitate is separated by filtration, washed and dried and then is recrystallized from tetrahydrofuran-n-hexane to give 3-(4-chlorobenzylidene)-1H-naphtho[2,1-b][1,4]thiazin-2(3H)-one (4.28 g). M.p. 277°-279° C.

(2) A mixture of the compound obtained above (4.0 g), 10% palladium on charcoal (2.0 g), tetrahydrofuran (200 ml) and ethanol (40 ml) is stirred under hydrogen gas under atmospheric pressure for 3 hours. After the reaction is completed, 10 % palladium-carbon is removed by filtration, and the solvent is distilled off. The residue is recrystallized from ethyl acetate-n-hexane to give 3-(4-chlorobenzyl)-1H-naphtho[2,1-b][1,4]thiazin-2(3H)-one (3.20 g). M.p. 185°-186° C.

EXAMPLE 72

To a mixture of 1-amino-2-naphthol (16.9 g), N,N-dimethylaniline (19.3 g) and tetrahydrofuran (200 ml) is added dropwise chloroacetyl chloride under ice cooling, and the mixture is stirred at the same temperature for one hour. To the reaction mixture is added ethyl acetate, and the ethyl acetate layer is washed, dried and distilled to remove the solvent. The resulting oil is dissolved in acetone (500 ml) and thereto is added potassium carbonate (75 g), and the mixture is refluxed for 2 hours, and acetone is distilled off. To the residue is added water, and the precipitate is separated by filtration, washed, dried and recrystallized from tetrahyrofuran to give 1H-naphtho[2,1-b][1,4]oxazin-2(3H)-one (13.1 g). M.p. 219°-220.5° C.

EXAMPLE 73

(1) To a solution of 3-(4-chlorophenyl)-1H-naphtho[2,1-b][1,4]thiazin-2(3H)-one (10.0 g) and 96% sodium hydroxide (1.96 g) in dimethylsulfoxide (150 ml) is added 1-bromo-3-chloropropane (6.78 g) under ice cooling, and the mixture is stirred at room temperature overnight. The reaction mixture is poured into water, and the mixture is extracted with ethyl acetate. The ethyl acetate layer is washed and distilled to remove the solvent. The residue is purified by silica gel column chromatography (eluent; n-hexane:ethyl acetate=5:1) and further is recrystallized from methanol to give 3-(4-chlorophenyl)-1-(3-chloropropyl)-1H-naphtho[2,1-b][1,4]thiazin-2(3H)-one (8.04 g). M.p. 110°-112.5° C.

(2) A mixture of the compound obtained above (1.0 g), diethylamine (3.72 g), sodium iodide (1.5 g), potassium carbonate (1.8 g) and acetone (50 ml) is refluxed overnight. The reaction mixture is distilled to remove the solvent, and to the residue is added water, and the mixture is extracted with ethyl acetate. The extract is distilled to remove the solvent. The residue is purified by silica gel column chromatography (eluent; chloroform:methanol=20:1) to give 3-(4-chlorophenyl)-1-[3-(diethylamino)propyl]-1H-naphtho[2,1-b][1,4]thiazin-2(3H)-one as oil.

To a solution of the compound obtained above in ether is added one equivalent of oxalic acid, and the resulting precipitate is separated by filtration and recrystallized from ethanol-diethyl ether to give 3-(4-chlorophenyl)-1-[3-(diethylamino)propyl]-1H-naphtho[2,1-b][1,4]thiazin-2(3H)-one oxalate (0.75 g). M.p. 190.5°-192.5° C. (dec.)

EXAMPLES 74 to 75

(1) The compound obtained in Example 24 is treated in the same manner as described in Example 73 to give the compounds as shown in Table 18.

TABLE 18

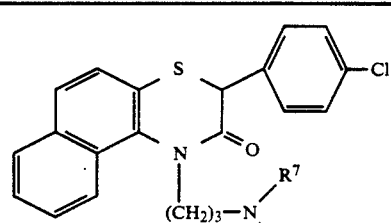

| Ex. No. | R$^7$ R$^8$ (N<) | M.p. etc. |
|---|---|---|
| 74 | —N(CH$_3$)(H) | hydrochloride: 224.5-227° C.*$^5$ |

TABLE 18-continued

[Structure: naphthalene fused with thiazine ring bearing 4-chlorophenyl group, N-(CH₂)₃-NR⁷R⁸ substituent]

| Ex. No. | N(R⁷)(R⁸) | M.p. etc. |
|---|---|---|
| 75 | —N⌒N (imidazolyl) | oxalate: 184.5–187.5° C. (dec.)*³ |

*³Recrystallized from ethanol
*⁵Recrystallized from ethanol-diethyl ether

EXAMPLE 76

A mixture of 3-(3-trifluoromethylphenyl)-1H-naphtho[2,1-b][1,4]thiazin-2(3H)-one (18.0 g), potassium carbonate (24.2 g), 3-(dimethylamino)propyl chloride hydrochloride (9.5 g), acetone (400 ml) and water (4 ml) is refluxed for 48 hours. The insoluble materials are filtered off and acetone is distilled off, and to the residue are added ethanol (200 ml) and 10 % hydrochloric acid (100 ml), and the mixture is refluxed for one hour. After ethanol is distilled off and the insoluble materials are filtered off, the resulting mixture is made alkaline with sodium hydrogen carbonate and extracted with ethyl acetate. The extract is distilled to remove the solvent to give 1-[3-(dimethylamino)-propyl]-3-(3-trifluoromethylphenyl)-1H-naphtho[2,1-b][1,4]-thiazin-2(3H)-one as oil.

Mass (m/z): 444 (M⁺)

To a solution of the compound obtained above in ether is added one equivalent of oxalic acid, and the resulting precipitate is separated by filtration and recrystallized from ethanol-diethyl ether to give 1-[3-(dimethylamino)propyl]-3-(3-trifluoromethylphenyl)-1H-naphtho[2,1-b][1,4]thiazin-2(3H)-one oxalate (16.23 g).

M.p. 130°–133° C.

EXAMPLES 77 to 87

The compounds obtained in Examples 24, 25B, 26, 28-29, 69-72 are treated in the same manner as described in Example 76 to give the compounds as shown in Tables 19 to 21.

TABLE 19

[Structure: naphthothiazinone with R⁵, R⁶ at α-carbon and N-A-N(CH₃)₂ on ring nitrogen]

| Ex. No. | R⁵ | R⁶ | A | M.p. |
|---|---|---|---|---|
| 77 | CH₃ | H | —(CH₂)₃— | oxalate: 163–165° C.*⁵ |
| 78 | CH₃ | CH₃ | —(CH₂)₃— | oxalate: 169–170° C.*⁵ |
| 79 | cyclohexyl (H) | H | —(CH₂)₃— | oxalate: 93° C. (dec.)*⁹ |
| 80 | 4-Cl-C₆H₄ | H | —(CH₂)₂— | oxalate: 220–221.5° C. (dec.)*⁷ |
| 81 | 4-Cl-C₆H₄ | H | —(CH₂)₃— | oxalate: 235–236.5° C. (dec.)*⁶ |
| 82 | 3-Cl-C₆H₄ | H | —(CH₂)₃— | oxalate: 190–192.5° C. (dec.)*³ |
| 83 | 4-F-C₆H₄ | H | —(CH₂)₂— | hydrochloride: 208.5–211.5° C.*⁹ |
| 84 | 4-F-C₆H₄ | H | —(CH₂)₃— | hydrochloride: 183–185.5° C.*⁵ |
| 85 | 4-Br-C₆H₄ | H | —(CH₂)₃— | hydrochloride: 219–222° C.*⁵ |

*³Recrystallized from ethanol
*⁵Recrystallized from ethanol-diethyl ether
*⁶Recrystallized from methanol-diethyl ether
*⁷Recrystallized from methanol
*⁹Recrystallized from ethyl acetate

TABLE 20

[Structure: naphtho-thiazine with R5, R7, R8, A-N substituents, oxalate]

| Ex. No. | R⁵ | A | NR⁷R⁸ | M.p. |
|---|---|---|---|---|
| 86 | —CH₂—C₆H₄—Cl | —(CH₂)₃— | —N(CH₃)₂ | 174–176° C. (dec.)*³ |

*³Recrystallized from ethanol

TABLE 21

[Structure: naphtho-oxazine with R5 and (CH₂)₃-N(CH₃)₂ ·HCl]

| Ex. No. | R⁵ | M.p. |
|---|---|---|
| 87 | H | 136.5–139.5° C.*⁵ |

*⁵Recrystallized from ethanol-diethyl ether

EXAMPLES 88

To a mixture of 3-(4-chlorophenyl)-1-[3-(methylamino)propyl]-1H-naphtho[2,1-b][1,4]thiazin-2(3H)-one (1.79 g), potassium carbonate (2.18 g) and acetone (50 ml) is added allyl bromide (0.65 g) under ice cooling, and the mixture is stirred at room temperature overnight. The insoluble materials are filtered off and acetone is distilled off, and the oily residue is purified by silica gel column chromatography (eluent, chloroform:methanol=20:1) to give 1-[3-(N-allyl-N-methylamino)-propyl]-3-(4-chlorophenyl)-1H-naphtho[2,1-b][1,4]thiazin-2(3H)-one as oil.

To a solution of the compound obtained above in ether is added one equivalent of oxalic acid, and the resulting precipitate is separated by filtration and recrystallized from ethanol-diethyl ether to give 1-[3-(N-allyl-N-methylamino)-propyl]-3-(4-chlorophenyl)-1H-naphtho[2,1-b][1,4]thiazin2(3H)-one oxalate (1.52 g).

M.p. 172.5°–175.5° C. (dec.)

EXAMPLE 89

The compound obtained in Example 74 is treated in the same manner as described in Example 88 to give 3-(4-chlorophenyl)-1-{3-[N-methyl-N-(2-propynyl)amino]propyl}-1H-naphtho[2,1-b][1,4]thiazin-2(3H)-one.

Oxalate: m.p. 166°–169° C (dec., recrystallized from ethanol-diethyl ether).

EXAMPLE 90

(1) To a solution of (±)-2-(4-chlorophenyl)-3,4-dihydro-2H-1,4-benzothiazine (10.01 g, 0.038 mole) in pyridine (150 ml) is added (S)-N-(2-naphthalenesulfonyl)-prolyl chloride (18.57 g, 0.057 mole), and the mixture is stirred at room temperature for 4 hours. To the reaction mixture is added ethyl acetate, and the mixture is washed with 5 % hydrochloric acid, water, aqueous sodium hydrogen carbonate solution, water and saline in this order, and the ethyl acetate layer is separated, dried over sodium sulfate and distilled to remove the solvent. The resulting caramel is subjected to silica gel column chromatography (hexane:ethyl acetate=5:1 - 3:1). From the fraction eluted first there is obtained (R)-2-(4-chlorophenyl)-4-[(S)-N-(2-naphthalenesulfonyl)prolyl]-3,4-dihydro-2H-1,4-benzothiazine (10.75 g, 51 %) as crystals. M.p. 147°–151° C.

Besides, from the fraction eluted subsequently there is obtained (S)-2-(4-chlorophenyl)-4-[(S)-N-(2-naphthalenesulfonyl)prolyl]-3,4-dihydro-2H-1,4-benzothiazine (7.58 g, 36%) as crystals. M.p. 171°–174.5° C.

(2) (R)-2-(4-Chlorophenyl)-4-[(S)-N-(2-naphthalenesulfonyl)prolyl]-3,4-dihydro-2H-1,4-benzothiazine (9.40 g, 0.017 mole) is suspended in ethanol-water (10:1, 188 ml), and thereto is added 86 % potassium hydroxide (11.2 g, 0.172 mole), and the mixture is refluxed for 30 minutes. The reaction mixture is poured into ice water and the mixture is extracted with ethyl acetate. The ethyl acetate layer is washed with water and saline, dried over sodium sulfate and distilled to remove the solvent. The residue is purified by silica gel column chromatography (CHCl₃) and thereafter recrystallized from ethyl acetate-hexane twice to give (R)-(+)-2-(4-chlorophenyl)-3,4-dihydro-2H-1,4-benzothiazine (2.61 g, 58%).

M.p. 151°–153° C.

[α]$_D^{20}$+38.0° (c=1.0, CHCl₃).

In the same manner as described above, (S)-2-(4-chlorophenyl)-4-[(S)-N-(2-naphthalenesulfonyl)prolyl]-3,4-dihydro-2H-1,4-benzothiazine (7.26 g, 0.0132 mole) is treated to give (S)-(-)-2-(4-chlorophenyl)-3,4-dihydro-2H-1,4-benzothiazine (2.45 g, 71 %). M.p. 151°–152.5° C.

[α]$_D^{20}$ −38.4° (c=1.0, CHCl₃).

(3) To a suspension of (R)-(+)-2-(4-chlorophenyl)-3,4-dihydro-2H-1,4-benzothiazine (1.30 g, 0.005 mole) and triethylamine (1.66 ml, 0.012 mole) in dichloromethane (16 ml) is added dropwise a solution of chloroacetyl chloride (0.79 ml, 0.01 mole) in dichloromethane (4 ml) under ice cooling, and the mixture is stirred at room temperature for 45 minutes. After the solvent is distilled off, to the residue are added ethyl acetate and water, and the ethyl acetate layer is washed with aqueous sodium hydrogen carbonate solution, water and saline, dried over sodium sulfate and distilled to remove the solvent to give (R)-4-chloroacetyl-2-(4-chlorophenyl)-3,4-dihydro-2H-1,4-benzothiazine (1.84 g) as caramel.

A mixture of the above-obtained compound, diethylamine (8 ml), sodium iodide (1.49 g, 0.01 mole) and tetrahydrofuran (24 ml) is stirred at room temperature for 30 minutes, and the volatiles are distilled off. To the residue are added ethyl acetate and aqueous sodium hydrogen carbonate solution, and the ethyl acetate layer is washed with water and saline, dried over sodium sulfate and distilled to remove the solvent. The residue is purified by silica gel column chromatography (CHCl3 methanol =50 : 1) to give (R)-(+)-2-(4-chlorophenyl)-4-diethylaminoacetyl-3,4-dihydro-2H-1,4-benzothiazine (1.74 g, 94 %) as caramel. Mass (m/z): 376, 374 (M+)

Oxalate (recrystallized from ethanol):
M.p. 133°-135° C. (decomp.)
$[\alpha]_D^{20}$ +111.9° (c=1.0, H2O).

In the same manner as described above, (S)-(-)-2-(4-chlorophenyl)-3,4-dihydro-2H-1,4-benzothiazine (1.30 g, 0.005 mole) is treated to give (S)-(-)-2-(4-chlorophenyl)-4-diethylaminoacetyl-3,4-dihydro-2H-1,4-benzothiazine (1.72 g, 92 %) as caramel. Mass (m/z): 376, 374 (M+)

Oxalate (recrystallized from ethanol): M.p. 133°-135° C. (decomp.)
$[\alpha]^{20}$ −112.6° (c=1.0, H2O).

EXAMPLE 91

(±)-2-(4-Chlorophenyl)-4-diethylaminoacetyl-3,4-dihydro-2H-1,4-benzothiazine (68.54 g, 0.183 mole) and (2S, 3S)-3-[(5-chloro-2-nitrophenyl)thio]-2-hydroxy-3-(4-methoxyphenyl)propionic acid (70.16 g, 0.183 mole) are dissolved in ethyl acetate (one liter), and the mixture is concentrated to about 500 ml and then allowed to stand. The resulting precipitate is separated by filtration and recrystallized from ethyl acetate twice to give a salt of (R)-isomer (30.80 g) as crystals. M.p. 153°-154° C.

The above-obtained compound is treated with diethyl ether-aqueous sodium hydrogen carbonate solution to convert into free base. The product is treated with HCl-ethanol to convert into hydrochloride. This product is recrystallized from ethanol-diethyl ether to give (R)-(+)-2-(4-chlorophenyl)-4-diethylaminoacetyl-3,4-dihydro-2H-1,4-benzothiazine hydrochloride (12.88 g, 17 %) as crystals.
M.p. 211.5°-212.5° C.
$[\alpha]_D^{20}$ +128.6° (c=1.0, H2O)

In the same manner as described above except that (2R, 3R)-3-[(5-chloro-2-nitrophenyl)thio]-2-hydroxy-3-(4-methoxyphenyl)propionic acid is used as the resoluting agent, there is obtained (S)-(-)-2-(4-chlorophenyl)-4-diethylaminoacetyl-3,4-dihydro-2H-1,4-benzothiazine hydrochloride.
M.p. 211°-212.5° C.
$[\alpha]_D^{20}$ −126.5° (c=1.0, H2O)

EXAMPLE 92

(1) A mixture of 3-(4-chlorophenyl)-2,3-dihydro-1H-naphtho[2,1-b][1,4]thiazine (25.0 g, 0.080 mole), (S)-N-(2-naphthalenesulfonyl)propyl chloride (25.96 g, 0.080 mole) and benzene (800 ml) is stirred at 60° C. for 24 hours. The insoluble materials are removed by filtration, and to the filtrate is added ethyl acetate, and the mixture is washed with 5 % hydrochloric acid, water, aqueous sodium hydrogen carbonate solution, water and saline in this order, and the ethyl acetate layer is dried over sodium sulfate and distilled to remove the solvent. The residue is subjected to silica gel column chromatography (ethyl acetate:hexane=1:3). From the fraction eluted first there is obtained (R)-3-(4-chlorophenyl)-1-[(S)-N-(2-naphthalenesulfonyl)prolyl]-2,3-dihydro1H-naphtho[2,1-b][1,4]thiazine (11.97 g, 25 %) as caramel.

Mass (m/z):600, 598 (M+)
IR $\gamma_{max}^{neat}$ cm$^{-1}$:1680

Besides, from the fraction eluted subsequently there is obtained (S)-3-(4-chlorophenyl)-1-[(S)-N-(2-naphthalenesulfonyl)prolyl]-2,3-dihydro-1H-naphtho[2,1-b][1,4]thiazine (12.13 g, 25.3 %) as crystals. M.p. 204°-205° C.

(2) A mixture of (R)-3-(4-chlorophenyl)-1-[(S)-N-(2-naphthalenesulfonyl)prolyl]-2,3-dihydro-1H-naphtho[2,1-b][1,4]thiazine (11.50 g, 0.019 mole), 86 % potassium hydroxide (15.0 g, 0.227 mole) and ethanol-water (10:1, 230 ml) is refluxed under argon for one hour. The reaction mixture is poured into ice water and the mixture is extracted with ethyl acetate. The ethyl acetate layer is washed with water and saline, dried over sodium sulfate and distilled to remove the solvent. The residue is purified by silica gel column chromatography (CHCl3) and thereafter recrystallized from ethyl acetate-hexane to give (R)-(+)-3-(4-chlorophenyl)- 2,3-dihydro-1H-naphtho[2,1-b][1,4]thiazine (3.74 g, 63%). M.p. 205°-206° C.
$[\alpha]_D^{20}$ +121.7° (c=1.0, CHC3).

In the same manner as described above, (S)-3-(4-chlorophenyl)-1-[(S)-N-(2-naphthalenesulfonyl)prolyl]-2,3-dihydro-1H-naphtho[2,1-b][1,4]thiazine (11.50 g, 0.019 mole) is treated to give (S)-(-)-3-(4-chlorophenyl)-2,3-dihydro-1H-naphtho[2,1-b][1,4]thiazine (3.09 g, 52%).
M.p. 206°-207° C.
$[\alpha]_D^{20}$ −121.1° (c=1.0, CHCl3).

(3) To a suspension of (R)-(+)-3-(4-chlorophenyl)-2,3-dihydro-1H-naphtho[2,1-b][1,4]thiazine (2.0 g, 0.0064 mole) and triethylamine (2.1 ml, 0.015 mole) in dichloromethane (30 ml) is added dropwise a solution of chloroacetyl chloride (1.0 ml, 0.0126 mole) in dichloromethane (5 ml) under ice cooling, and the mixture is stirred at room temperature for 45 minutes. After the volatiles are distilled off, to the residue are added ethyl acetate and water, and the ethyl acetate layer is washed with aqueous sodium hydrogen carbonate solution, water and saline, dried over sodium sulfate and distilled to remove the solvent. The residue is purified by silica gel column chromatography (ethyl acetate:hexane=1:4) to give (R)-1-chloroacetyl-3-(4-chlorophenyl)-2,3-dihydro1H-naphtho[2,1-b][1,4]thiazine (2.40 g, 96%) as caramel.

A mixture of the above-obtained compound (1.20 g, 0.0031 mole), sodium iodide (0.93 g, 0.0062 mole) and 10% solution of dimethylamine in tetrahydrofuran (25 ml) is stirred at room temperature for 5.5 hours, and the solvent is distilled off. To the residue are added ethyl acetate and aqueous sodium hydrogen carbonate solution, and the ethyl acetate layer is washed with water and saline, dried over sodium sulfate and distilled to remove the solvent. The residue is purified by silica gel column chromatography (CHCl3:methanol=50:1) to give (R)-(+)-3-(4-chlorophenyl)-1-dimethylaminoacetyl-2,3-dihydro-1H-naphtho[2,1-b][1,4]thiazine (1.15 g, 94 %) as caramel. Mass (m/z): 398, 396 (M+)

Oxalate (recrystallized from methanol-diethyl ether): M.p. 215.5°-216.5° C. (decomp.) $[\alpha]_D^{20}$ +297.0° (c=1.0, DMF)

In the same manner as described above, (S)-(-)-3-(4-chlorophenyl)-2,3-dihydro-1H-naphtho[2,1-b][1,4]thiazine (0.98 g, 0.0031 mole) is treated to give (S)-(-)-3-(4-chlorophenyl)-1-dimethylaminoacetyl-2,3-dihydro-1H-naphtho[2,1-b][1,4]-thiazine (1.19 g, 95.0 %) as caramel. Mass (m/z): 398, 396 (M+)

Oxalate (recrystallized from methanol-diethyl ether): M.p. 215°-216.5° C. (decomp.) $[\alpha]_D^{20}$ −296.6° (c=1.0, DMF)

EXAMPLE 93

The corresponding starting material is treated in the same manner as described in Example 92, there is obtained (R)-(+)- and (S)-(-)-3-(4-chlorophenyl)-1-diethylaminoacetyl-2,3-dihydro- 1H-naphtho[2,1-b][1,4]thiazine oxalate.

(R)-(+)-isomer (oxalate: recrystallized from acetone): M.p. 137°-140° C. $[\alpha]_D^{20}$ +322.7° (c=1.0, methanol)

(S)-(-)-isomer (oxalate: recrystallized from acetone): M.p. 138°-140.5° C. $[\alpha]_D^{20}$ −321.7° (c=1.0, methanol)

EXAMPLE 94

(±)-1-Dimethylaminopropyl-3-(3-trifluoromethylphenyl)-1H-naphtho[2,1-b][1,4]thiazin-2(3H)-one (7.53 g, 0.0169 mole) and (2R, 3R)-3-[(5-chloro-2-nitrophenyl)thio]-2-hydroxy-3-(4-methoxyphenyl)propionic acid (6.50 g, 0.0169 mole) are dissolved in ethyl acetate, and the mixture is concentrated and thereto is added diethyl ether, and the mixture is allowed to stand overnight. The resulting precipitate is separated by filtration and recrystallized from ethyl acetate twice to give a salt of (+)-isomer (3.04 g, 22%) as crystals. M.p. 147°-148° C.

The above-obtained compound (2.80 g) is stirred in diethyl ether-aqueous sodium hydrogen carbonate solution. The diethyl ether layer is washed with water, dried and distilled to remove the solvent to give (+)-1-dimethylaminopropyl-3-(3-trifluoromethylphenyl)-1H-naphtho[2,1-b][1,4]thiazin-2(3H)-one (1.42 g, 94%) as oil.

Mass (m/z) 444 (M+)
IR $\gamma_{max}^{neat}$ cm$^{-1}$:1670
$[\alpha]_D^{20}$ +80.1° (c=1.0, CHCl$_3$).
Oxalate:
M.p. 101°-104° C.
$[\alpha]_D^{20}$ +115.9° (c=1.0, methanol)

In the same manner as described above except that (2S, 3S)-3-[(5-chloro-2-nitrophenyl)thio]-2-hydroxy-3-(4-methoxyphenyl)propionic acid is used as the resolving agent, there is obtained (-)-1-dimethylaminopropyl-3-(3-trifluoromethylphenyl)-1H-naphtho[2,1-b][1,4]thiazin-2(3H)-one as oil.

Mass (m/z):444 (M+)
IR $\gamma_{max}^{neat}$ cm$^{-1}$:1670
$[\alpha]_D^{20}$ −80.5° (c=1.0, CHCl$_3$).
Oxalate:
M.p. 102°-106° C.
$[\alpha]_D^{20}$ −118.6° (c=1.0, methanol)

PREPARATION OF STARTING MATERIALS

Reference Example 1

To a suspension of 2-aminothiophenol (12.6 g) and sodium acetate (23.6 g) in ethanol (150 ml) is added methyl α-bromo-4-fluorophenylacetate (23.6 g), and the mixture is stirred at room temperature overnight. After the solvent is distilled off, water is added to the residue. The resulting precipitate is separated by filtration, washed, dried, and then recrystallized from tetrahydrofuran-n-hexane to give 2-(4-fluorophenyl)-3-oxo-3,4-dihydro-2H-1,4-benzothiazine (21.7 g) as crystals. M.p. 216°-219° C.

Reference Examples 2 to 4

The corresponding starting materials are treated in the same manner as described in Reference Example 1 to give the compounds as shown in Table 22.

TABLE 22

| Ref. Ex. No. | $R^5$ | M.p. (solvent for recrystal.) |
|---|---|---|
| 2 | 3-CF$_3$-C$_6$H$_4$ | 159-161.5° C. (tetrahydrofuran-n-hexane) |
| 3 | 2,4-Cl$_2$-C$_6$H$_3$ | 227-229° C. (tetrahydrofuran-n-hexane) |
| 4 | 4-CH$_3$-C$_6$H$_4$ | 199-201° C. (tetrahydrofuran-n-hexane) |

Reference Example 5

To a solution of 2-amino-5-chlorothiophenol (4.49 g) in ethanol (30 ml) is added 96 % potassium hydroxide (1.63 g), and the mixture is distilled to remove ethanol. The resulting solid material is suspended in toluene (70 ml) and thereto is added methyl °-bromo-4-chlorophenylacetate (7.38 g), and the mixture is refluxed overnight. The reaction mixture is concentrated, and the resulting precipitate is separated by filtration, washed, dried, and then recrystallized from tetrahydrofuran-n-hexane to give 7-chloro-2-(4-chlorophenyl)-3-oxo-3,4-dihydro-2H-1,4-benzothiazine (6.58 g) as crystals. M.p. 230°-233.5° C.

Reference Example 6

To a solution of 2-chloro-3-oxo-3,4-dihydro-2H-1,4-benzothiazine (9.38 g) and thiophene (7.91 g) in methylene chloride (250 ml) is added in portions stannic chloride (12. 2 g) at 0° to 5° C. After stirring at the same temperature for 45 minutes, the mixture is poured into ice water, and the organic layer is separated. The aqueous layer is extracted with ethyl acetate, and the ethyl acetate layer is combined with the above organic layer and distilled to remove the solvent. The resulting solid material is recrystallized from ethanol to give 3-oxo-2-(2-thienyl)-3,4-dihydro-2H-1,4-benzothiazine (8.17 g) as crystals.

M.p. 174°-177° C.

Reference Example 7

The corresponding starting materials are treated in the same manner as described in Reference Example 6 to give the compound as shown in Table 23.

TABLE 23

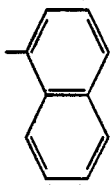

| Ref. Ex. No. | $R^5$ | M.p. (solvent for recrystal.) |
|---|---|---|
| 7 | 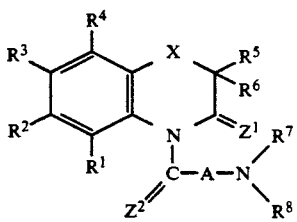 | 246.5-247.5° C. (tetrahydrofurn-ethanol) |

Reference Example 8

To a solution of 2-aminophenol (13.5 g) in ethyl acetate (150 ml) is added a solution of sodium hydrogen carbonate (15 g) in water (300 ml), and to the mixture is added dropwise a solution of o-bromo-4-chlorophenylacetyl chloride (32.2 g) in toluene with vigorous stirring under ice cooling. After the mixture is stirred at room temperature for one hour, the solvent in the organic layer is distilled off and the residue is dissolved in acetone. To the solution is added potassium carbonate (20 g), and the mixture is stirred at room temperature overnight. The solvent is distilled off and to the residue is added water. The mixture is extracted with ethyl acetate. The ethyl acetate layer is washed, dried and distilled to remove the solvent, and the residue is recrystallized from ethyl acetate-n-hexane to give 2-(4-chlorophenyl)-3-oxo-3,4-dihyro-2H-1,4-benzoxazine (24.0 g) as crystals. M.p. 180.5°-181.5° C.

What is claimed is:

1. A compound which is a thiazine or oxazine derivative of the following formula [I]:

[I]

wherein $R^1$ and $R^2$ form a naphthalene ring together with the benzene ring; $R^3$ and $R^4$ are both hydrogen atoms, or one of them is a halogen atom and the other is a hydrogen atom; X is a sulfur atom or an oxygen atom; $R^5$ and $R^6$ are the same or different and are each i) a hydrogen atom, ii) lower alkyl, iii) cycloalkyl, iv) substituted phenyl, v) naphthyl, vi) lower alkyl which is substituted by a substituted or unsubstituted phenyl, or vii) a sulfur-containing monoheterocyclic group; one of $Z^1$ and $Z^2$ is an oxygen atom and the other is a pair of hydrogen atoms; A is lower alkylene; $R^7$ and $R^8$ are the same or different and are each i) a hydrogen atom, ii) lower alkyl, iii) lower alkenyl, iv) lower alkynyl, or v) lower alkyl which is substituted by a substituted or unsubstituted phenyl, or $R^7$ and $R^8$ form together with the adjacent nitrogen atom a nitrogen-containing monoheterocyclic group and $R^2$ are hydrogen; or a pharmaceutically acceptable salt thereof.

2. The compound according to claim 1, wherein $R^3$ and $R^4$ are both hydrogen atoms; $R^5$ and $R^6$ are the same or different and are each i) a hydrogen atom, ii) lower alkyl, iii) cycloalkyl, iv) phenyl having 1 or 2 substituents selected from the group consisting of a halogen atom, trihalogeno(lower)alkyl and lower alkyl, v) naphthyl, or vi) thienyl; and $R^7$ and $R^8$ are the same or different and are each i) a hydrogen atom, ii) lower alkyl, iii) lower alkenyl, or iv) lower alkynyl, or $R^7$ and $R^8$ form together with the adjacent nitrogen atom a nitrogen-containing monoheterocyclic group selected from the group consisting of morpholinyl, pyrrolidinyl and piperidyl.

3. The compound according to claim 1, wherein one of $R^5$ and $R^6$ is a hydrogen atom and the other is i) a cycloalkyl, ii) phenyl having 1 or 2 substituents selected from the group consisting of a halogen atom, trihalogeno(lower)alkyl and lower alkyl, iii) naphthyl, or iv) halogenophenyl-substituted lower alkyl; and $R^7$ and $R^8$ are the same or different and are each i) a hydrogen atom, ii) lower alkyl, iii) lower alkenyl, iv) lower alkynyl, or v) a lower alkyl substituted by di(lower)alkoxyphenyl, or $R^7$ and $R^8$ form together with the adjacent nitrogen atom a nitrogen-containing monoheterocyclic group selected from the group consisting of morpholinyl, pyrrolidinyl, piperidinyl and imidazolyl.

4. The compound according to claim 1, wherein $R^3$ and $R^4$ are both hydrogen atoms; one of $R^5$ and $R^6$ is a hydrogen atom and the other is i) cycloalkyl, ii) phenyl having 1 or 2 substituents selected from the group consisting of a halogen atom, trihalogeno(lower)alkyl and lower alkyl, or iii) naphthyl; and $R^7$ and $R^8$ are the same or different and are each i) a hydrogen atom, ii) lower alkyl, iii) lower alkenyl, or iv) lower alkynyl, or $R^7$ and $R^8$ form together with the adjacent nitrogen atom piperidyl.

5. The compound according to claim 4, wherein X is a sulfur atom.

6. The compound according to claim 5, wherein one of $R^5$ and $R^6$ is hydrogen atom and the other is halogenophenyl dihalogenophenyl or a trihalogeno(lower)alkylphenyl, and $R^7$ and $R^8$ are the same or different and are each lower alkyl.

7. The compound according to claim 5, wherein one of $R^5$ and $R^6$ is hydrogen atom and the other is chlorophenyl, dichlorophenyl or trifluoromethylphenyl, and $R^7$ and $R^8$ are both methyl or ethyl.

8. 3-(4-Chlorophenyl)-1-(diethylamino)acetyl-2,3-dihydro-1H-naphtho[2,1-b][1,4]thiazine or a pharmaceutically acceptable salt thereof.

9. 1-[3-(dimethylamino)propyl]-3-(3-trifluoromethylphenyl)-1H-naphtho[2,1-b][1,4]thiazin-2(3H)-one or a pharmaceutically acceptable salt thereof.

10. 3-[(2,4-dichloro)phenyl]-1-(dimethylamino)acetyl-2,3-dihydro-1H-naphtho[2,1-b][1,4]thiazine or a pharmaceutically acceptable salt thereof.

11. A pharmaceutical composition which comprises a therapeutically effective amount of a thiazine or oxazine derivative of the formula as set forth in claim 1 in admixture of a conventional pharmaceutically acceptable carrier or diluent.

12. A method for the prophylaxis or treatment of ischemic encephalopathia in a warm-blooded animal which comprises administering an effective amount of a thiazine or oxazine administering an effective amount of a thiazine or oxazine derivative of the formula as set forth in claim 1 to said warm-blooded animal suffering from the disease.

* * * * *